United States Patent
Niwa et al.

(10) Patent No.: US 8,740,977 B2
(45) Date of Patent: Jun. 3, 2014

(54) INTRAOCULAR LENS INSERTION TOOL

(75) Inventors: Kazuharu Niwa, Nagoya (JP);
Masayoshi Tanaka, Nagoya (JP);
Yasuhiko Suzuki, Inazawa (JP)

(73) Assignee: Kowa Company, Ltd., Nagoya-shi (JP)

(*) Notice: Subject to any disclaimer, the term of this patent is extended or adjusted under 35 U.S.C. 154(b) by 0 days.

(21) Appl. No.: 13/129,258

(22) PCT Filed: Dec. 1, 2008

(86) PCT No.: PCT/JP2008/003546
§ 371 (c)(1),
(2), (4) Date: May 13, 2011

(87) PCT Pub. No.: WO2010/064275
PCT Pub. Date: Jun. 10, 2010

(65) Prior Publication Data
US 2011/0224677 A1 Sep. 15, 2011

(51) Int. Cl.
*A61F 2/16* (2006.01)
*A61F 9/007* (2006.01)

(52) U.S. Cl.
USPC ........................................ 623/6.12; 606/107

(58) Field of Classification Search
USPC ................................ 606/107; 623/6.11, 6.12
See application file for complete search history.

(56) References Cited

U.S. PATENT DOCUMENTS

| | | | | |
|---|---|---|---|---|
| 5,928,245 | A * | 7/1999 | Wolf et al. | 606/107 |
| 6,858,033 | B2 * | 2/2005 | Kobayashi | 606/107 |

(Continued)

FOREIGN PATENT DOCUMENTS

| | | |
|---|---|---|
| JP | A 11-506356 | 6/1999 |
| JP | A 2003-070829 | 3/2003 |

(Continued)

OTHER PUBLICATIONS

International Preliminary Report on Patentability issued in International Patent Application No. PCT/JP2008/003546 dated Jun. 7, 2011.

(Continued)

*Primary Examiner* — Ryan Severson
*Assistant Examiner* — Anh Dang
(74) *Attorney, Agent, or Firm* — Oliff PLC

(57) ABSTRACT

An intraocular lens insertion tool is presented. An introductory part in an insertion cylinder is provided, at a widthwise central portion of a bottom surface, with a central protrusion which extends in an axial direction of a tool body and protrudes toward an upper surface to get in contact with a center portion of a rear surface of an optical zone of an intraocular lens. The upper surface is provided, at its both widthwise ends, with a pair of lateral protrusions, which extend in the axial direction of the tool body and protrude toward the bottom surface to get in contact with both ends of a front surface of the optical zone of the intraocular lens. A lens pressing face of a plunging member is formed with a dimension spanning from the bottom surface to the upper surface at a tip end section of the insertion cylinder.

10 Claims, 14 Drawing Sheets

(56) References Cited

U.S. PATENT DOCUMENTS

| | | | |
|---|---|---|---|
| 7,037,312 B2 | 5/2006 | Kikuchi et al. | |
| 7,156,854 B2 | 1/2007 | Brown et al. | |
| 2003/0050647 A1* | 3/2003 | Brady | 606/107 |
| 2004/0243141 A1* | 12/2004 | Brown et al. | 606/107 |
| 2005/0149058 A1* | 7/2005 | Lin et al. | 606/107 |

FOREIGN PATENT DOCUMENTS

| | | |
|---|---|---|
| JP | A 2003-533273 | 11/2003 |
| JP | A 2004-351196 | 12/2004 |
| JP | A 2007-190360 | 8/2007 |
| JP | A 2007-526091 | 9/2007 |
| JP | A 2008-220953 | 9/2008 |
| WO | WO 2008/029498 A1 | 3/2008 |

OTHER PUBLICATIONS

International Search Report issued in PCT/JP2008/003546, mailed Feb. 10, 2009.

Apr. 23, 2013 Office Action issued in Japanese Patent Application No. 2010-541143 (with partial translation).

Apr. 28, 2013 Office Action issued in Chinese Patent Application No. 200880132178.4 (with partial translation).

Chinese Office Action issued in Chinese Patent Application No. 200880132178.4 dated Dec. 2, 2013 (w/ translation).

* cited by examiner

A−A

B−B

C−C

INTRAOCULAR LENS INSERTION TOOL

TECHNICAL FIELD

This invention relates to an intraocular lens insertion tool used for inserting an intraocular lens into the eye.

BACKGROUND ART

Conventionally, in cataract surgery and other operations, a method has been adopted wherein a crystalline lens is extracted and removed from the capsule through an incision made on ocular tissues such as the cornea (sclera) and anterior lens capsule, and thereafter, an intraocular lens is inserted into the eye via the above incision to be set in the capsule in lieu of the removed lens.

In such operations using an intraocular lens, insertion tools for intraocular lenses such as those described in Patent Documents 1 and 2 are commonly used. In general, these insertion tools for intraocular lenses are used to place an intraocular lens within the lens capsule by means of inserting the tip opening of an insertion cylinder located at the tip of the tool body through an incision and pushing out the intraocular lens in a compactly deformed condition from the tip opening of the insertion cylinder, which unfolds out within the lens capsule with its own restoring force. Using this type of insertion tool allows us not only to minimize the incision and save time and effort for operations, but also to reduce the risk of postoperative astigmatism and infections.

Meanwhile, the intraocular lenses often have different shapes between their front and back sides such as those, for example, with the haptic tilting toward the front surface of the lens (cornea side) in order to suppress secondary cataract by pushing the optical zone against the rear interior (vitreous side) of the lens capsule. For this reason, the intraocular lens requires its front and back sides placed correctly in the capsule.

However, conventional insertion tools for intraocular lens had a problem that the front and back sides of the intraocular lens tend to be flipped within the capsule. Therefore, the operator needed to displace the insertion tool in the rotational direction by an amount that assumes a counterturn before inserting it into the eye in order to avoid difficult work of reversing the turn of the intraocular lens in the right direction within the capsule after the operation, or to turn the insertion tool as soon as the intraocular lens unfolds inside the capsule after being pushed out of the insertion tool. However, such a manipulation is not easy, requiring skilled hands. Especially, the operator was hard-pressed to work carefully not to cause any damage to the incision and the like in turning the insertion tool.

Patent Document 1: JP-A-2003-70829
Patent Document 2: JP-A-2004-351196

DISCLOSURE OF THE INVENTION

Problem the Invention Attempts to Solve

Now, this invention was made under the background of the above situation, aiming at solving the problems by providing an intraocular lens insertion tool with a novel structure capable of placing the front and back sides of the intraocular lens more securely in the right direction.

Means for Solving the Problem

As a result of devoted studies to solve the above problems, the inventor has come to recognize that the cause of the counterturn of the intraocular lens is its unfolding action following the direction of the tip of the haptics within the capsule. In other words, the intraocular lens bent within the nozzle of the insertion tool is generally made to have a pair of haptics projecting from the optical zone unfold out in the front-back direction of the send-out direction. One of the haptics that unfolds out to the front direction is sent into the capsule before the optical zone via the tip opening of the insertion tool and has already been in contact with the interior surface of the capsule at the time when the optical zone is sent into the capsule.

In this situation, the intraocular lens folded within the insertion tool is substantially rolled up after passing through the insertion cylinder as disclosed, for example, in Patent Document 1. Therefore, the haptic that unfolds out from the periphery of the optical zone was sometimes pushed out of the insertion tool in a reverse condition and was made in contact with the interior surface of the capsule in a state reversed from the normal position. Then, it has come to a point where a prediction was made that the optical zone turns in reverse and unfolds out within the capsule as did the haptic that was made in contact with the interior surface of the capsule in a reverse condition by having the optical zone unfold out around a restraint center, that is, the point where the haptics sent earlier are in contact with the interior surface of the capsule. Therefore, the inventor was able to complete this invention based on such new knowledge.

Namely, a first mode of this invention provides an intraocular lens insertion tool including a tool body in a form of a cylinder adapted to contain an intraocular lens, a plunging member to be assembled to the tool body by being inserted therein in an axial direction from a back, a stage on which the intraocular lens is adapted to be placed provided at a middle of the tool body in the axial direction, and an insertion cylinder of tapered shape on a tip side of the stage in the axial direction, the plunging member being adapted to be plunged in order to move forward the intraocular lens placed on the stage in the axial direction so that the intraocular lens is deformed compactly and pushed out through the insertion cylinder into an eye, the intraocular lens insertion tool being characterized in that: the insertion cylinder includes a bottom surface continuous from a lens platform of the stage, and an upper surface placed opposite the bottom surface; a central protrusion is provided at a central portion in a width direction of the tool body in the bottom surface of an introductory part on a side of the stage of the insertion cylinder so as to extend in the axial direction of the tool body and be made to protrude toward the upper surface to get in contact with a center portion of a rear surface of an optical zone of the intraocular lens sent into the insertion cylinder; a pair of lateral protrusions are provided at both ends in the width direction of the tool body in the upper surface of the introductory part so as to extend in the axial direction of the tool body and be made to protrude toward the bottom surface to get in contact with both ends of a front surface of the optical zone of the intraocular lens sent into the insertion cylinder; and the plunging member has a lens pressing surface formed at a tip face thereof in the axial direction with a dimension spanning from the bottom surface to the upper surface at a tip end section of the insertion cylinder.

According to the present mode, once the intraocular lens is sent into the introductory part of the insertion cylinder, the central protrusion is made in contact with a radial line at the center in the rear surface of the optical zone of the intraocular lens, and at the same time, the lateral protrusion is made in contact with both ends of a radial line perpendicular to the aforementioned radial line at the center in the front surface of the optical zone of the lens. This causes pressing force to exert toward the upper surface along the radial line at the center in the rear surface of the optical zone, and at the same time, in the front surface of the optical zone, causes pressing force to exert toward the bottom surface at both ends of the radial line perpendicular to the aforementioned radial line at the center sandwiching it in between. As a result, the optical zone of the intraocular lens is subject to initial deformation in a mountain shape wherein the front surface of the optical zone is made convex at the introductory part, and is rolled up even more compact within the insertion cylinder.

During such a push-out process, the intraocular lens in the insertion cylinder is made to develop a state called "tucking" wherein the tip of the haptic positioned toward the push-out or plunging direction is tucked into the rolled-up optical zone. Then, by having the intraocular lens pushed out of the insertion cylinder under such state of tucking, the optical zone and haptic are sent into the capsule almost simultaneously, and the whole intraocular lens including these optical zone and haptic are almost simultaneously unfolded within the capsule. As a result, it is now possible to restrain the tip of the haptic from abutting against the interior surface of the capsule prior to the optical zone and to reduce the risk of counterturn of the optical zone caused by the haptic's abutting against the interior surface of the capsule, thus enabling more secure placement of the intraocular lens at the normal position within the capsule.

In addition, the haptics of the intraocular lens are generally set protruded from outer periphery thereof in the form of a pair of tentacles, and their tips constitute free ends curving in an approximate direction of the lens's circumference. Also, when the intraocular lens is curved with the insertion tool, the protrusions of the haptics are set at a position away from the curve's center line (mountain or valley line) of the lens. For this reason, when the intraocular lens is curved, the entire haptics get twisted around the curve's center line of the lens. As a result, the tips of the haptics end up protruding toward the curve's center line (mountain or valley line side) of the lens. Therefore, in case of valley line, the tips of the haptics protrude toward the rear side of the lens, which is the lower side of the insertion tool so that, if the haptics unfold prior to the optical zone, the tips of the haptics are likely to get in contact with the rear side of the lens capsule. Since the haptics are supposed to securely support the lens by abutting against the front side of the lens capsule (intracapsular front), the abutting of the haptics against the rear surface of the capsule may adversely affect stable positioning of the intraocular lens. On the contrary, according to this invention, making the intraocular lens mountain folded allows the tips of the haptics to protrude toward the lens's front side, that is, the upper side of the insertion tool. Therefore, even if the haptic unfolds and protrudes out prior to the optical zone during insertion, the unfolded haptic ends up abutting against the front side of the lens capsule (intracapsular front), which should normally happen, thus making it easy to avoid adversely affecting the positioning of the intraocular lens. At the same time, since the haptic is twisted around the curve's center line of the lens, if the tucking occurs in a state of mountain fold, the haptic is bent in such a way that its front side (corresponding to the front side of the lens) comes forward in the plunging direction. On the contrary, in a state of valley fold, since the twisting direction of the haptic in line with the intraocular lens's curving is reversed, the haptic is bent in such a way that its rear side (corresponding to the rear side of the lens) comes forward in the plunging direction during tucking. Therefore, even if the haptic unfolds and protrudes out prior to the optical zone during insertion, the tip of the haptic unfolds with its front side facing forward in the traveling direction in case of mountain fold. Consequently, the unfolded haptic is made to abut against the front side of the lens capsule, which should normally happen, while its front side that should abut against the front side of the lens capsule at the normal position is made to abut against the front side of the lens capsule. Thus, unfolding of the optical zone following the haptic that is made in contact with the lens capsule at the normal position allows the optical zone to unfold more securely at the normal position.

As explained above, this invention focuses on the above tucking phenomenon, and by being actively used, makes it possible to place the intraocular lens more securely at the normal position. According to this invention, tucking is considered to be made more securely by means of adopting a special form mentioned above and imposing curved deformation in a state of mountain fold on the intraocular lens. In other words, many conventional insertion tools give small deformation to the intraocular lens in a state of valley fold wherein the front surface of the optical zone is made concave. The major reason for it is that, since the plunging member is made movable along the lens platform of the tool body or the bottom surface of the insertion cylinder, the pressure bearing surface of the intraocular lens is positioned on such bottom surface. However, in order for the tip of the haptics to get into the optical zone that has been rolled up in a state of valley fold, the tips of the haptics need not only to move along the stage or the subsequent bottom surface of the insertion cylinder, but also to get into the optical zone so as to run over the optical zone placed thereon.

On the other hand, in case of mountain fold wherein the front surface of the optical zone is made convex, the tips of the haptics are able to get into the space formed below the optical zone as it is by just moving over the stage and the subsequent bottom surface of the insertion cylinder without any need for running over the optical zone. In other words, a space (gap) is formed between the optical zone and insertion cylinder as the roll-up gradually progresses, while the tips of the haptics are sent into this space to be enclosed therein, thus enabling the haptics to get into the optical zone more easily than in the case of valley fold. Also, the mountain-folded intraocular lens has the center of its optical zone distanced from the bottom. In this situation, according to this invention, since the lens pressing surface of the plunging member is made in a dimension spanning from the bottom surface to upper surface at the tip of the insertion cylinder, the intraocular lens is significantly deformed in a state of mountain fold so that the contact between the lens pressing surface and the optical zone is maintained even at the tip where the center of the optical zone is distanced from the bottom surface so as to reach the upper surface, thus allowing to securely maintain the push-out of the intraocular lens. For this reason, "the lens pressing surface formed with a dimension spanning from the bottom surface to upper surface at the tip of the insertion cylinder" according to this invention is good enough to be able to stably press on both the peripheral surface of the intraocular lens placed on the bottom surface of the insertion cylinder and the peripheral surface of the intraocular lens placed on the upper surface of the insertion cylinder in a mountain fold, and there can be a gap between the lens pressing surface and the top or bottom surface to the extent not interfering with the pressing of the intraocular lens. More specifically, there is no problem with having a gap between the lens pressing surface of the plunging member and the top or bottom surface at the tip of the insertion cylinder to the extent that the gap is smaller than the thickness of the outer periphery of the intraocular lens, but most preferably, the dimension of the gap to the bottom or upper surface is set at no more than half the thickness of the outer periphery of the intraocular lens.

The central and lateral protrusions can each be formed in plurality. In other words, as mentioned below, the central protrusion can be formed, for example, by a pair of protrusions that sandwiches the plunging member, or a pair of lateral protrusions can each be formed by multiple protrusions with the protruding dimension made larger as it gets closer to the outer periphery of the intraocular lens adapted to get in contact with them. Also, the central and lateral protrusions do not have to extend exactly parallel to the central axis of the tool body all the way long. For example, tips of the pair of lateral protrusions in the plunging direction of the intraocular lens can be close to each other to fit the tapered shape of the insertion cylinder, or the facing distance between the lateral protrusions (separation distance in the width direction of the tool body) can be made larger than the outer diameter of the optical zone at the entrance of the introductory part and made gradually reduced toward the tip of the insertion cylinder.

Also, the central and lateral protrusions are good enough if they are formed at least at the introductory part of the insertion cylinder and can cause initial deformation of the intraocular lens in a form of mountain fold, or for example, they can extend further forward from the introductory part in the plunging direction, or further backward therefrom in the same direction. Also, they do not have to be formed continuously over the entire length of the introductory part but can be formed partially in the longitudinal direction thereof.

A second mode of this invention provides the insertion tool according to the above first mode, wherein a tip opening of the insertion cylinder has an inclined shape wherein the upper surface protrudes beyond the bottom surface in the axial direction of the tool body.

The present mode can maintain the state of tucking for a longer period of time. That is, in case of a simple form opening wherein the edge of the tip opening stretches out in the width direction of the tool body, unfolding of the part to be exposed starts immediately because the entire side of rolled-up optical zone is exposed all at once, thus posing a risk that the haptic is likely to get unfolded prior to the optical zone. On the contrary, according to the present mode, since the upper surface is made to protrude more than the bottom surface, the exposed part at the bottom surface can be maintained in a state of deformation inside the upper surface and the surroundings. This allows us to maintain a state of deformation, that is what caused the tucking according to this invention, for a longer period of time, and prevent the haptic from unfolding prior to the optical zone more effectively, and place the intraocular lens at the normal position more securely.

In the present mode, more preferably, an mode can be adopted in which the tilt angle of the tip opening relative to the surface perpendicular to the axis of the insertion cylinder is formed larger at the base side than the tip side. This allows the area enclosing the intraocular lens to be longer in the axial direction, thus enabling to maintain the tucking state of the intraocular lens for a longer period of time.

A third mode of this invention provides the intraocular lens insertion tool according to the first or second mode, wherein a separation distance between the pair of lateral protrusions at their protruded tips in the width direction of the tool body is smaller than an outer diameter of the front surface of the optical zone of the intraocular lens at a tip of the lateral protrusions in a plunging direction of the intraocular lens, and a separation distance between the central protrusion and the lateral protrusions in a facing direction of the upper surface and the bottom surface is smaller than a separation distance between an outer periphery of the front surface of the optical zone of the intraocular lens and an apex of the rear surface of the optical zone in a direction of an optical axis at a tip of the central protrusion in the plunging direction of the intraocular lens. This allows each of the central and lateral protrusions to be made in contact with the rear center of the optical zone and both front ends of the optical zone, respectively, of the intraocular lens more securely, thus causing initial deformation more securely in a form of mountain fold.

A fourth mode of this invention provides the intraocular lens insertion tool according to any one of the first to third modes, wherein a reduction rate of an area per length in the axial direction at the insertion cylinder is varied along the axial direction, and an intermediate section in the axial direction of the insertion cylinder is formed with the largest reduction rate of the area, while a width of the bottom surface at the intermediate section is made to gradually vary from a dimension larger than the outer diameter of the intraocular lens down to smaller dimensions, and the central protrusion and the pair of lateral protrusions are formed to extend in the axial direction from an axial end on a side of larger width at the intermediate section, the introductory part being configured to include a part of the intermediate section.

According to the present mode, at a stage when deformation of the intraocular lens is relatively easy, the intermediate section with a large area reduction rate can cause significant deformation per length in the axial direction. This allows the intraocular lens to undergo deformation more rapidly while reducing the risk of damage to the lens. Because of the introductory part formed to include part of the intermediate section, deformation of the intraocular lens in mountain fold caused by the central and lateral protrusions can be produced more securely at the stage when deformation is relatively easy.

A fifth mode of this invention provides the intraocular lens insertion tool according to the fourth mode, wherein tips of the central and lateral protrusions in the plunging direction of the intraocular lens are positioned at the intermediate section.

In the present mode, more preferably, the tips of the central and lateral protrusions can be set at a position where the width of the bottom surface is made smaller than the outer diameter of the intraocular lens at the intermediate section. This allows the intraocular lens to undergo deformation more securely in a mountain fold. In addition, in the present mode, the tip side of the intermediate section in the insertion cylinder is made to be a non-forming region of the central and lateral protrusions. This reduces the risk of unnecessarily deforming the intraocular lens or increasing the pressing pressure to damage the intraocular lens due to the central and lateral protrusions stretching all the way to the tip of the insertion cylinder.

A sixth mode of this invention provides the intraocular lens insertion tool according to any one of the first to fifth modes, wherein a curvature radius of the bottom surface is larger than that of the upper surface at the introductory part.

According to the present mode, due to the curvature made different between the bottom and upper surfaces, unnecessary rotation of the intraocular lens can be restricted in the introductory part. Also, since the upper surface is curved more acutely than the bottom surface, the shape of the lens in the introductory part can be made similar to that of the optical zone made to be a mountain fold in the introductory part, restricting any excess space from appearing while restricting the intraocular lens from slipping into the excess space, thus causing deformation of the intraocular lens more securely in a form of mountain fold.

In the present mode, more preferably as a seventh mode of this invention, the intraocular lens insertion tool according to the sixth mode, wherein the bottom surface at the introductory part is a flat plane, that is, the curvature radius of the bottom surface is made infinite. This can prevent deformation of the optical zone in valley fold more effectively and produce mountain fold deformation more securely.

An eighth mode of this invention provides the intraocular lens insertion tool according to any one of the first to seventh modes, wherein a rear end of the central protrusion in the plunging direction of the intraocular lens extends to the lens platform.

According to the present mode, upon placing the intraocular lens on the lens platform of the stage, the central protrusion can be abutted against the rear center of the optical zone. This allows the intraocular lens to be made in a state of mountain fold from the start of the push-out, more securely producing initial deformation in mountain fold. At the same time, a risk of having the optical zone entangled with the central protrusion, like in the case of having the optical zone made in contact with the central protrusion in the middle of a push-out operation, can be avoided.

A ninth mode of this invention provides the intraocular lens insertion tool according to any one of the first through eighth modes, wherein the central protrusion guides the plunging member in the axial direction of the tool body by getting in contact with the plunging member.

According to the present mode, the mechanism of guiding the plunging member can be realized by best utilizing the central protrusion. This allows the plunging member to move stably in the axial direction of the tool body, thus enabling more stable push-put of the intraocular lens. Besides, the number of parts can be reduced and the shape design of the tool body simplified by best utilizing the central protrusion as a mechanism of guiding such plunging member.

As a specific structure of the present mode, a concave groove, for example, that fits in with the central protrusion can be provided to the plunging member. Alternatively, in a tenth mode of the present intraocular lens insertion tool, the central protrusion comprises a pair of guiderails, positioned on both sides of the plunging member in the width direction of the tool body, and at tips of the guiderails in the plunging direction of the intraocular lens, a separation distance between the guiderails at their protruded tips in the width direction of the tool body is smaller than a separation distance between the pair of lateral protrusions at their protruded tips in the same direction.

This allows the plunging member, sandwiched between a pair of guiderails, to be guided in the axial direction of the tool body. As evident from the present mode, the central protrusion of this invention can be configured in plurality.

KEYS TO SYMBOLS

10: Insertion tool, 12: Tool body, 14: Plunger, 16: Intraocular lens, 18: Optical zone, 20: Haptic, 22: Front surface of the optical zone, 24: Rear surface of the optical zone, 34: Stage, 66: Nozzle part, 80: Introductory part, 82: Send-out part, 84: Bottom surface, 86: Upper surface, 90: Guiderails, 92: Siderails, 112: Lens pressing surface.

BEST MODE FOR CARRYING OUT THE INVENTION

To further illustrate this invention more specifically, its embodiments will be described in detail below referring to each Figure.

Figure 1:
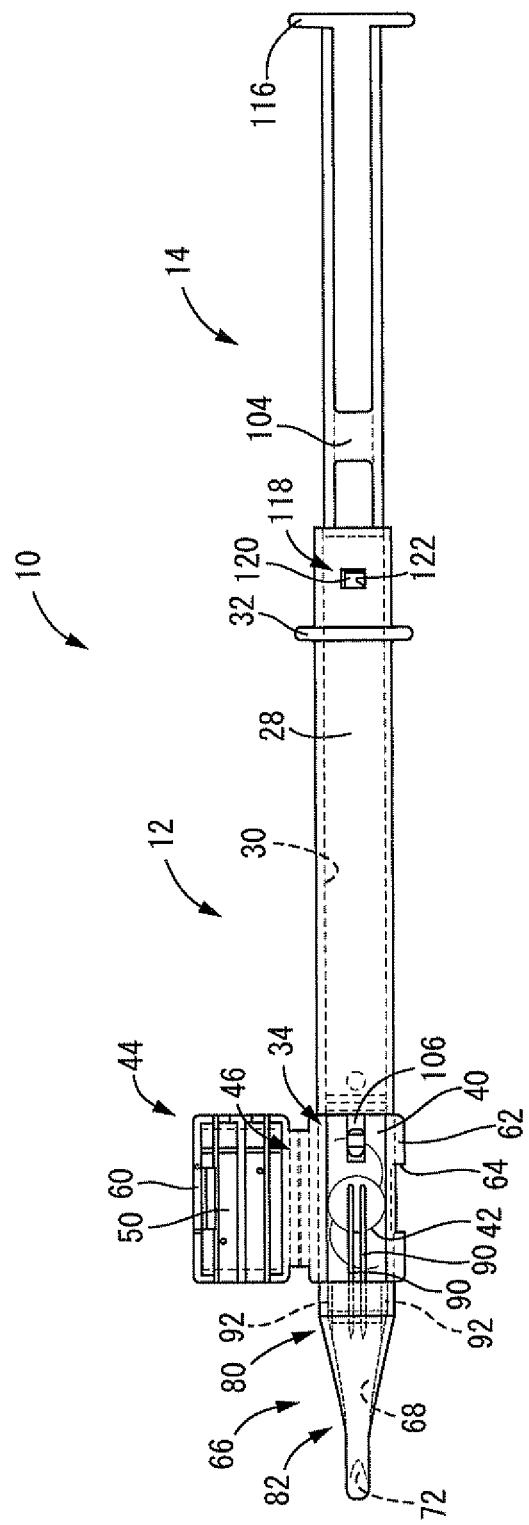
FIG. 1 is a plan view of an intraocular lens insertion tool as one preferred embodiment of this invention.
Figure 2:
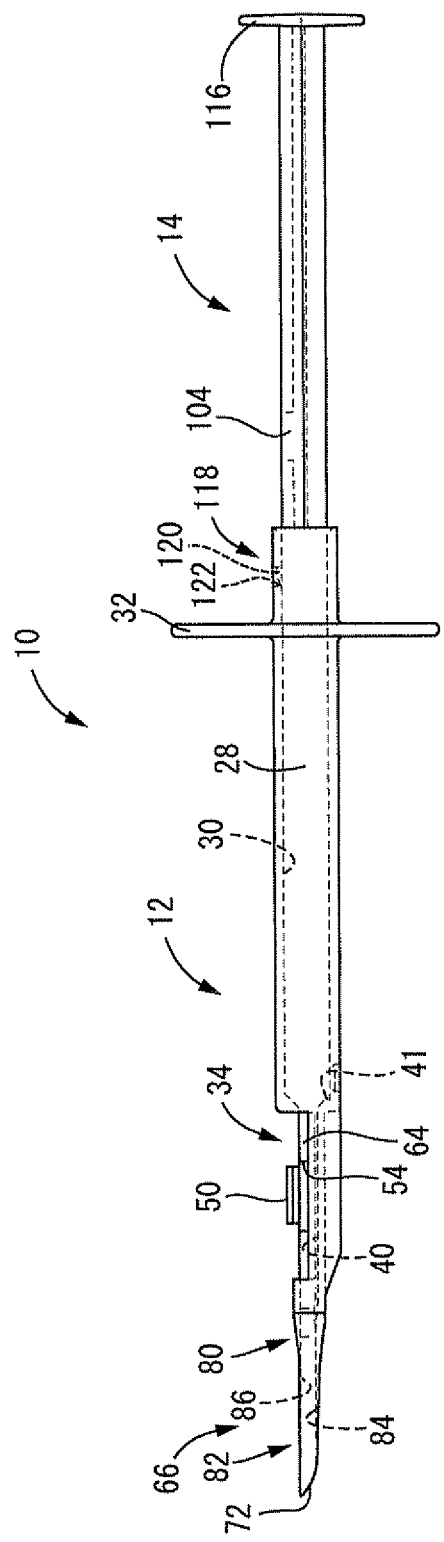
FIG. 2 is a side elevation of the same insertion tool.

First of all, FIGS. 1 and 2 show an intraocular lens insertion tool 10 as one of the embodiments of this invention. The insertion tool 10 contains an intraocular lens 16 described later within a tool body 12 in an approximate shape of a cylinder with a pass-through hole inside and open front and back ends, and is configured with a plunger 14 inserted therein as a plunging member. In the following descriptions, the "front" of the insertion tool 10 means a direction in which the plunger 14 is pushed out (left side in FIG. 1), and the "up-down direction" means that of FIG. 2. In addition, the "left-right direction" means that of the insertion tool 10 seen from behind (up is right and down is left in FIG. 1), and the "width direction" means this left-right direction unless otherwise specified. Also, the "front" of the eye means the cornea side and the "rear" means the vitreous side in the descriptions below.

Figure 3:
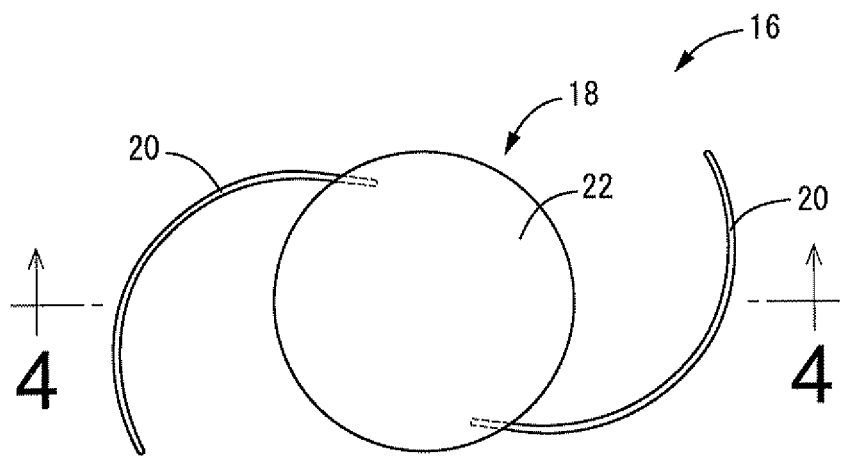
FIG. 3 is a front elevation diagram showing an intraocular lens to be contained in the same insertion tool.
Figure 4:
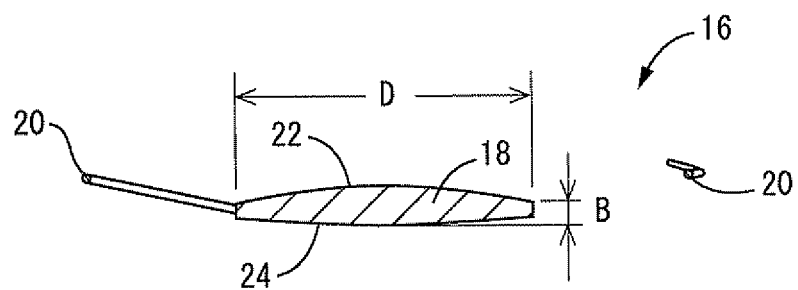
FIG. 4 is a sectional diagram taken along line 4-4 in FIG. 3.

FIGS. 3 and 4 show diagrams of the intraocular lens 16 contained in the insertion tool 10 of the present embodiment. The intraocular lens 16 is an intraocular lens that has been known to the public and comprises an optical zone 18 that offers optical characteristics and a pair of haptics 20 that are made to protrude from the optical zone 18 toward the periphery. And, the optical zone 18 is supported by the haptics 20 to be arranged in a certain position within the lens capsule. In this situation, the optical zone 18, being arranged within the lens capsule, is equipped with a front surface of the optical zone 22 and a rear surface of the optical zone 24, and the curvature rates of the front and rear surfaces of the optical zone 22, 24 are set properly in consideration of required optical characteristics and the like. Such optical zone 18 is formed, as has been known to the public, with soft materials that are easy to deform such as PHEMA (polyhydroxyethylmethacrylate).

Also, the pair of haptics 20 are formed in a shape of thin strings and are made to protrude toward opposite directions to each other from opposite peripheral points in the diametrical direction of the optical zone 18, while being made in a form of a reverse S seen from front wherein the tip of each protrusion is positioned to wrap around the optical zone 18 in the same direction. Additionally, these haptics 20 are slightly tilted toward the front of the lens as they separate away from the optical zone 18 and let the rear surface of the optical zone 24 pushed against the inside surface of the capsule while being contained therein, thus exerting effects of preventing adhesion of the intraocular lens to the iris and inhibiting secondary cataract. In this situation, as the intraocular lens 16 of the present embodiment, it is made as so called "three-piece intraocular lens" wherein the haptics 20 are formed with a different material from those of the optical zone 18, although it is of course possible to adopt the insertion tool 10 of the present embodiment for so called "one-piece intraocular lens" and the like wherein the haptics 20 are formed with the same material as those of the optical zone 18.

On the other hand, the tool body 12 comprises a cylinder main body 28 in an approximate shape of a cylinder. Inside the cylinder main body 28, a through-hole 30 that runs through in an approximate cross-sectional shape of a rectangle in the axial direction is formed. Also, a plate part 32 is integrally formed extending in the direction perpendicular to the extending direction of the cylinder main body 28 at the location slightly forward of the rear end of the cylinder main body 28.

Figure 5:
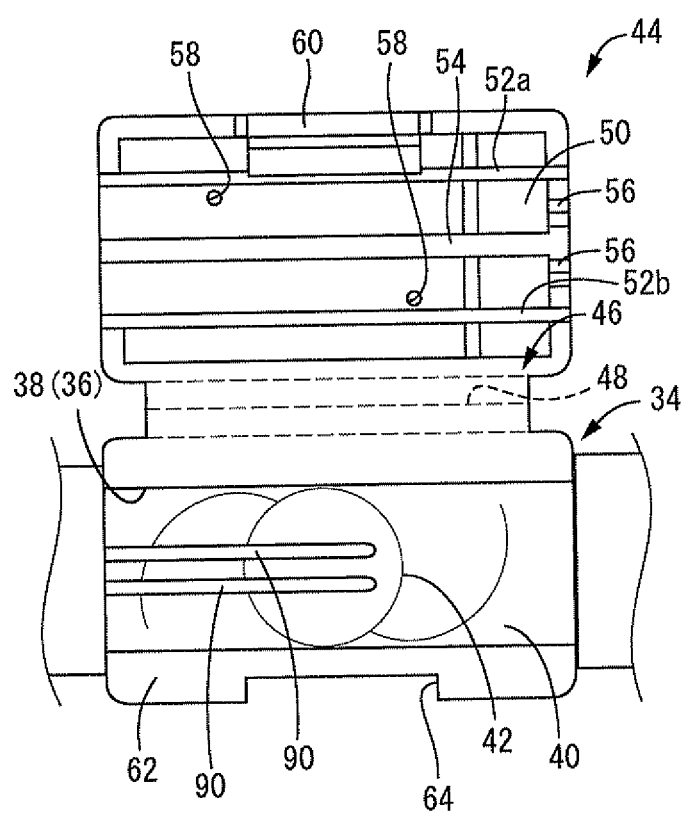
FIG. 5 is a plan view of a stage of the insertion tool shown in FIG. 1.

Furthermore, in front of the cylinder main body 28 of the tool body 12, a stage 34 is formed. FIG. 5 shows the stage 34. On the stage 34, a concave groove 36 is formed extending in the axial direction with a slightly larger width than the diameter of the optical zone 18 of the intraocular lens 16. The concave groove 36 is formed in a slightly larger longitudinal dimension in the axial direction than the maximum width of the intraocular lens 16 including the haptics 20 and 20 (left-right dimension in FIG. 3) in a state of containment in the stage 34.

In this situation, the concave groove 36 has an opening 38 that opens up to the top, while a lens platform 40 is formed on its bottom surface. The lens platform 40 is made to be a flat plane that has a slightly larger width than the minimum width (up-down dimension in FIG. 3) of the intraocular lens 16 and a slightly larger length in the axial direction than the maximum width (left-right dimension in FIG. 3) of the intraocular lens 16. The position of the lens platform 40 is set higher than the bottom surface of the through-hole 30 of the cylinder main body 28, and at the front end thereof, a lower wall 41 (see FIG. 2) that connects to the rear end of the lens platform 40 is formed. Thus, the concave groove 36 is in communication with the through-hole 30 and its width is made approximately the same as that of the through-hole 30. Also, at the lens platform 40, a mold 42 is formed in a shape of an intraocular lens indicating the placement direction of the intraocular lens 16 on the stage 34. In such mold 42, the extending direction of the haptics is made so as to form a reverse S with the front surface of the optical zone 22 of the intraocular lens 16 positioned upward when seen from above.

Now, on the lateral side of the concave groove 36 (right side in the present embodiment), a cover section 44 is integrally formed with the tool body 12 as a cap thereof. The cover section 44 has approximately the same dimension as that of the concave groove 36 in the axial direction, while being formed with a width slightly larger than that of the concave groove 36. Additionally, the cover section 44 is connected to the tool body 12 by a hinge section 46 in an approximate shape of a thin plate formed by the upper end of the stage 34 extending sideways (right side in the present embodiment).

The hinge section 46 is made the thinnest at a bend 48 that extends in the axial direction of the tool body 12 at approximately the center in the width direction, and made bendable at the bend 48. This allows the cover section 44 to be overlapped on the concave groove 36, by bending the hinge section 46, to cover the opening 38.

In addition, on an opposite plane 50 facing the lens platform 40 at the cover section 44, a pair of right and left guide plates 52a and 52b are integrally formed with protrusions. These guide plates 52a and 52b are formed across the entire cover section 44 in the axial direction keeping a distance to each other slightly smaller than the width of the concave groove 36. Meanwhile, the outer periphery of the opposite plane 50 is formed in sufficient thickness all the way around, and the right and left guide plates 52a and 52b are made further protruded from such outer periphery of the opposite plane 50.

Also, at the approximate center of the right and left guide plates 52a and 52b on the opposite plane 50, a central guide plate 54 is integrally formed extending parallel to the right and left guide plates 52a and 52b in the axial direction of the tool body 12. The central guide plate 54 is made in a height that stands out slightly over the outer periphery of the opposite plane 50 formed in sufficient thickness and integrally formed so as to extend out of the outer periphery across the entire length of the opposite plane 50 in the axial direction. Moreover, at the joint connecting the outer periphery of the opposite plane 50 and the rear end of the central guide plate 54 in the axial direction, a pair of guiding protrusions 56 are formed on both sides of the central guide plate 54. The guiding protrusions 56 are integrally formed to protrude from the outer periphery of the opposite plane 50 in an approximate cross-sectional shape of a triangle, and their protruding dimensions are approximately the same as those of the right and left guide plates 52a and 52b.

Also, in the cover section 44, a liquid inlet 58 that runs across the thickness is formed in an appropriate number and at appropriate locations, through which a proper lubricant can be poured into the tool body 12 as needed.

In addition, at the edge opposite the hinge section 46 in the cover section 44, an engaging tab 60 is formed protruded, while at the tip of the opening opposite the cover section 44 of the stage 34, a protruded edge 62 is formed protruding in the opposite direction of the cover section 44, and at a position corresponding to the engaging tab 60 in such protruded edge 62, an engaging notch 64 is formed.

Figure 6:
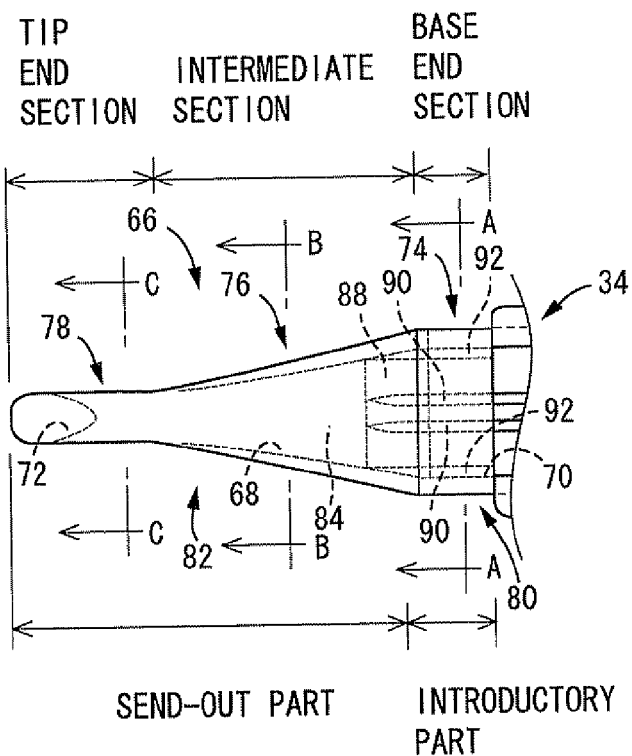
FIG. 6 is a plan view of an insertion cylinder of the same insertion tool.
Figure 7:
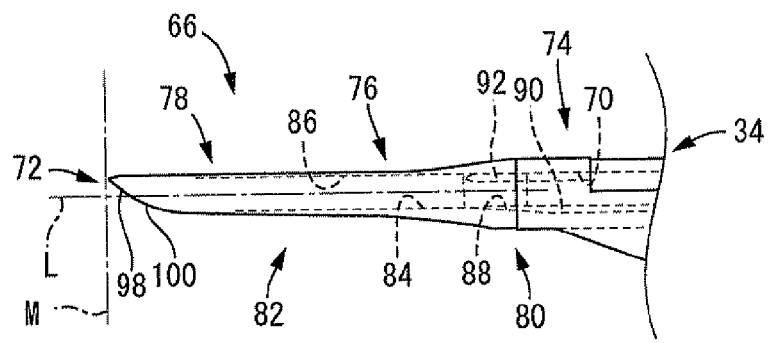
FIG. 7 is a side elevation of the same insertion cylinder.

Furthermore, in front of the stage 34 at the tip of the tool body 12 in the axial direction, a nozzle part 66 is integrally formed as an insertion cylinder. FIGS. 6 and 7 show the nozzle part 66. The nozzle part 66, as a whole, is formed in an outer shape that tapers off toward the tip from the base end on the stage 34 side in the extending direction (to the left in FIG. 6), while a through-hole 68 that runs across the entire length in the extending direction is formed. And, one of the ends of the through-hole is made to be a base opening 70 that communicates with the stage 34, while the other end opposite the base opening 70 is made to be a tip opening 72.

Especially, the nozzle part 66 in the present embodiment, as shown in FIG. 6, comprises a base end section 74, an intermediate section 76 and a tip end section 78. The base end section 74 is formed with approximately constant cross-section extending in the axial direction. Meanwhile, the intermediate section 76 and tip end section 78 are in a form that tapers off toward the tip with the area of cross-section perpendicular to the axis reduced at about a constant ratio. In this situation, the reduction rate of the area per length in the axial direction in the intermediate section 76 is made larger than that of the tip end section 78, and the reduction rate of the area per length in the axial direction in the nozzle part 66 is made maximum in the intermediate section 76, whereas the area reduction rate is set small enough in the tip end section 78 so that approximately constant cross-section extends out straight.

Also, in the through-hole 68, a bottom surface 84 that continues all the way from the lens platform 40 without any bump and an upper surface 86 placed opposite above the bottom surface 84 are formed. Besides, the width of the bottom surface 84 at the base end section 74 is set equal to that of the lens platform 40 at the stage 34 and is made constant at a slightly larger width than the outer diameter of the optical zone 18 of the intraocular lens 16, while in the intermediate section 76, it varies gradually from a slightly larger width than the outer diameter of the optical zone 18 to smaller widths as it moves from the side of the base end section 74 toward the tip end section 78. And in the present embodiment at the through-hole 68 that gradually reduces its width toward the tip, the section with larger width than the outer diameter of the optical zone 18 of the intraocular lens 16 is made to be an introductory part 80, and the section with smaller width a send-out part 82, wherein the introductory part 80 is formed to include the base end section 74 as well as the section where the width of the through-hole 68 is larger than the outer diameter of the optical zone 18 in the intermediate section 76. Therefore, the intraocular lens 16 is made difficult to enter into the send-out part 82 in a free state without deformation, and the optical zone 18 is subject to flexural deformation once it is sent into the send-out part 82.

Figure 8A:
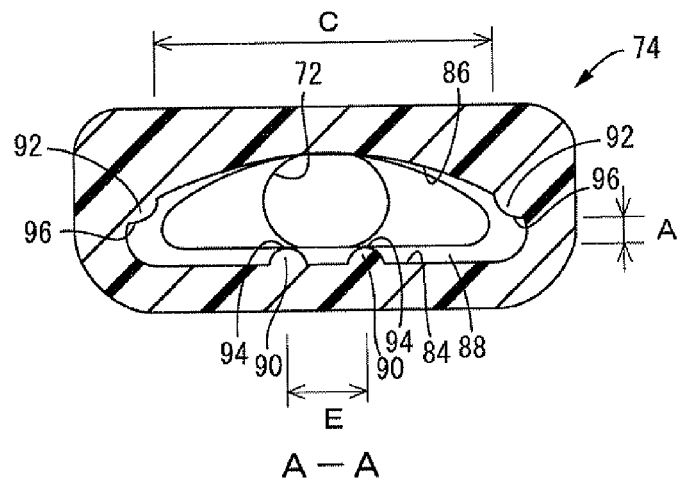
FIGS. 8A, 8B, 8C are cross sectional views taken along line A-A, B-B and C-C in FIG. 6.
Figure 8B:
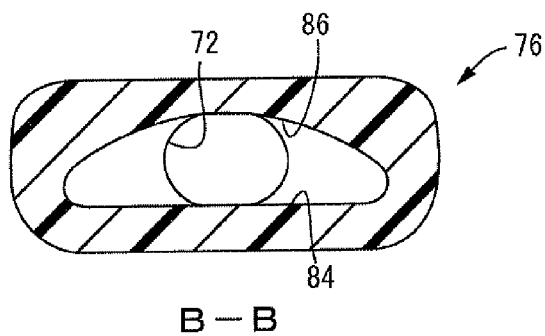
Figure 8C:
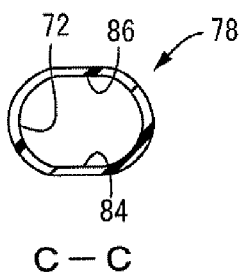

Additionally, as shown in FIG. 8, the through-hole 68 is formed in a shape of half-moon or a round rice cake, which is gradually deformed into an approximate shape of an oval toward the tip opening 72. This allows the curvature radius of the bottom surface 84 in the cross-section perpendicular to the axis of the tool body 12 is made larger than that of the upper surface 86 in the introductory part 80, and especially in the present embodiment, the bottom surface 84 in the introductory part 80 is made to be a flat plane with an infinite curvature radius. Meanwhile, on the bottom surface 84 at the tip of the introductory part 80, an incline 88 that is gradually tilted upward as it moves forward in the axial direction is formed, while the bottom surface 84 of the through-hole 68 is made to be a stepped surface including the incline 88. On the other hand, the upper surface 86 of the through-hole 68 is made to be a flat plane without any step across the entire length in the axial direction.

At the center in the width direction on the bottom surface 84 in such introductory part 80, a pair of guiderails 90 are formed as central protrusions that protrude toward the upper surface 86. Each guiderail 90 is made to be a protrusion that protrudes out straight in a given dimension in the axial direction of the tool body 12. Especially, each guiderail 90 in the present embodiment has its tip placed at the tip of the incline 88 at a position slightly beyond the tip of the introductory part 80. Particularly, the tip of the guiderail 90 extends over to a position where the width of the bottom surface 84 gets smaller than the outer diameter of the optical zone 18 of the intraocular lens 16 in the plunging direction of the lens in the intermediate section 76. On the other hand, the rear end of the guiderail 90 extends out to the lens platform 40 beyond the rear end of the introductory part 80 and placed at a position slightly forward of a lens pressing surface 112 of the plunger 14 located in the initial position explained later. Here, especially in the present embodiment, the tip of the guiderail 90 is made to get the same height and position as the bottom surface 84 as if being gradually sucked up into the bottom surface 84 toward the tip as the incline 88 gets higher as it goes toward the front in the axial direction. Meanwhile, the rear end of the guiderail 90 is, more preferably, made to be an incline that gradually protrudes out from the lens platform 40 toward the upper surface 86 in the extending direction of the guiderail 90. This can reduce the risk of having the plunger 14 entangled with the guiderail 90 or having the intraocular lens 16 entangled in the case where the lens 16 runs over the guiderail 90 in the middle of a push-out operation due to the rear end of the guiderail 90 placed in front of the lens platform 40.

These pair of guiderails 90 are formed almost parallel to each other with a given distance in between in the width direction on the bottom surface 84 sandwiching the center thereof in the width direction, and the separation distance between the pair of guiderails 90 in the width direction is, more preferably, made approximately equal to the width of a shaft section 106 (explained later) of the plunger 14, and in the present embodiment, made slightly smaller than the width of the shaft section 106. This allows the pair of guiderails 90 in the present embodiment to be located on both sides of the shaft section 106 in the width direction of the tool body 12 during the push-in operation of the plunger 14. In addition, especially in the present embodiment, the pair of guiderails 90 are formed almost parallel to each other, and the separation distance between them in the width direction of the tool body 12 are set approximately constant across the entire length of the guiderails 90.

In addition, at both ends of the upper surface 86 in the width direction of the introductory part 80, siderails 92 are formed as a pair of lateral protrusions extending out toward the bottom surface 84. The siderail 92 is made to extend straight in a given dimension in the axial direction of the tool body 12. Especially the siderail 92 in the present embodiment has its tip placed at approximately the same position as the tip of the guiderail 90 in the axial direction of the nozzle part 66 slightly beyond the introductory part 80, while the rear end is placed at the position of the base opening 70 to include the upper surface 86 of the introductory part 80. Especially in the present embodiment, the tip of the siderail 92 is made to become flush with the interior surface of the through-hole 68 as if being gradually sucked up into the interior of the through-hole 68 as it goes toward the tip. Meanwhile, the rear end of the siderail 92, more preferably, is made to be an incline that gradually protrudes out from the upper surface 86 toward the bottom surface 84 in the extending direction of the siderail 92. This reduces the risk of having the intraocular lens 16 entangled with the siderail 92. Also, especially in the present embodiment, the pair of siderails 92 are formed almost parallel to each other, and the separation distance between these pair of siderails 92 in the width direction of the tool body 12 is set approximately constant across the entire length of the siderail 92.

In this situation, as shown in FIGS. 4 and 8, the separation distance A between a protruded tip 94 of the guiderail 90 directing toward the upper surface 86 and a protruded tip 96 of the siderail 92 directed toward the bottom surface 84 in the facing direction of the upper surface 86 and bottom surface 84 (up-down direction in FIG. 8) is made smaller than the separation distance B between the outer periphery of the front surface of the optical zone 22 in the intraocular lens 16 and the apex of the rear surface of the optical zone 24 in the direction of the optical axis of the lens (up-down direction in FIG. 4) at least at the tip of the guiderail 90 and siderail 92 in the axial direction of the tool body 12. Moreover, the separation distance C between the pair of siderails 92 at the protruded tip 96 in the width direction of the tool body 12 (left-right direction in FIG. 8) is made smaller than the outer diameter D of the front surface of the optical zone 22 of the intraocular lens 16 at least at the tip of the siderail 92 in the axial direction of the tool body 12. And especially in the present embodiment, the central protrusion is configured of a pair of guiderails 90, and the separation distance E between the pair of guiderails 90 at the protruded tip 94 in the width direction of the tool body 12 (left-right direction in FIG. 8) is made smaller than the separation distance C between the pair of siderails 92 at the protruded tip 96 in the width direction of the tool body 12 at least at the tip of the guiderail 90 in the axial direction of the tool body 12. And especially in the present embodiment, since the pair of guiderails 90 and pair of siderails 92 are each formed approximately parallel to each other, the above relations of A<B and E<C are set across the entire length where the guiderail 90 and siderail 92 face each other, while the relation of C<D is set across the entire length of the siderail 92.

Under these circumstances, the separation distance A between the protruded tip 94 of the guiderail 90 and the protruded tip 96 of the siderail 92 is, more preferably, set as 0.05 mm≤A≤1.0 mm. Most likely, if such separation distance A is smaller than 0.05 mm, the abutting pressure imposed on the intraocular lens 16 is increased to pose a risk of not being able to evenly bend the parts abutting against both siderails 92, whereas, if the separation distance A is larger than 1.0 mm, there is a risk of having the intraocular lens 16 fail to contact the siderails 92.

Also, the separation distance B between the outer periphery of the front surface of the optical zone 22 and the apex of the rear surface of the optical zone 24 in the direction of the optical axis of the lens in the intraocular lens 16 can adopt appropriate values within the range of upper and lower limits according to the standard of the intraocular lens, but more preferably, it is set as 0.1 mm≤B≤1.2 mm. Most likely, it is because, if such separation distance B is smaller than 0.1 mm, keeping the shape of the intraocular lens 16 gets more difficult, whereas, if the separation distance B is larger than 1.2 mm, there is a risk of having difficulties in bending the lens.

Also, the separation distance C between the pair of siderails 92 in the width direction of the tool body 12 at the protruded tips 96 is, more preferably, set as 3.0 mm≤C≤6.4 mm. Most likely, it is because, if the separation distance C is smaller than 3.0 mm, the space for mountain folding the intraocular lens 16 gets smaller to pose a risk of increasing the sliding resistance of the intraocular lens 16 against the interior surface of the through-hole 68, whereas, if the separation distance C is larger than 6.4 mm, there is a risk of having the intraocular lens 16 fail to contact the siderails 92 on both sides.

Besides, the outer diameter D of the front surface of the optical zone 22 of the intraocular lens 16 can adopt appropriate values within the range of upper and lower limits according to the standard of the intraocular lens, but more preferably, it is set as 5.5 mm≤D≤6.5 mm. Most likely, it is because, if the outer diameter D of the front surface of the optical zone 22 is smaller than 5.5 mm, problems such as glaring tend to occur, whereas, if the outer diameter D is larger than 6.5 mm, the incision to insert the lens into the lens capsule becomes larger.

Furthermore, the separation distance E between the pair of guiderails 90 in the width direction of the tool body 12 at the protruded tip 94 is, more preferably, set as 0.5 mm≤E≤4.0 mm. Most likely, it is because, if such separation distance E is smaller than 0.5 mm, the pair of guiderails 90 virtually turn into a single protrusion extending in the axial direction at the center of the bottom surface 84, posing a risk of interfering with the movement of the plunger 14, whereas, if the separation distance E is larger than 4.0 mm, they get too far away from the center of the rear surface of the optical zone 24, posing a risk of failing to exert pressure upward at the center thereof.

Meanwhile, as shown in FIG. 7, the tip opening 72 is formed at the tip of the nozzle part 66, wherein the tip opening 72 is made to be an incline tilted from a plane M perpendicular to the central axis L of the nozzle part 66 in a side view by having the upper surface 86 made to protrude beyond the bottom surface 84. Especially at the tip opening 72 of the present embodiment, a linear section 98 with approximately a constant tilt angle is formed on the side closer to the upper surface 86, whereas, on the side closer to the bottom surface 84, a curving section 100 that continues from the linear section 98 is formed having a larger tilt angle than the linear section 98 wherein such tilt angle changes more rapidly as it gets closer to the bottom surface 84. This makes the tip opening 72 in the present embodiment in an approximate curve shape that shows a convex toward the outside of the nozzle part 66 in the side view. However, the tip opening 72, in the side view, can be configured solely by a linear section or a curve section across the entire length, or otherwise, a shape made of curves with continuously varying ratio of curvature can be adopted.

As explained above, the tool body 12 in the present embodiment is made an integrally molded product having the cylinder main body 28, stage 34, cover section 44, and nozzle part 66. The tool body 12 is formed with an optically transparent member so that the intraocular lens 16 contained in the tool body 12 is visible through the cover section 44 even under the condition where the opening 38 of the stage 34 is covered with the cover section 44.

Figure 9:
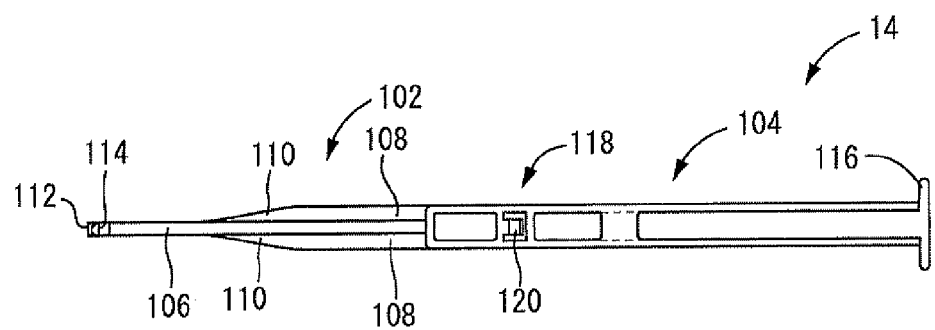
FIG. 9 is a plan view of a plunging member in the insertion tool shown in FIG. 1.
Figure 10:
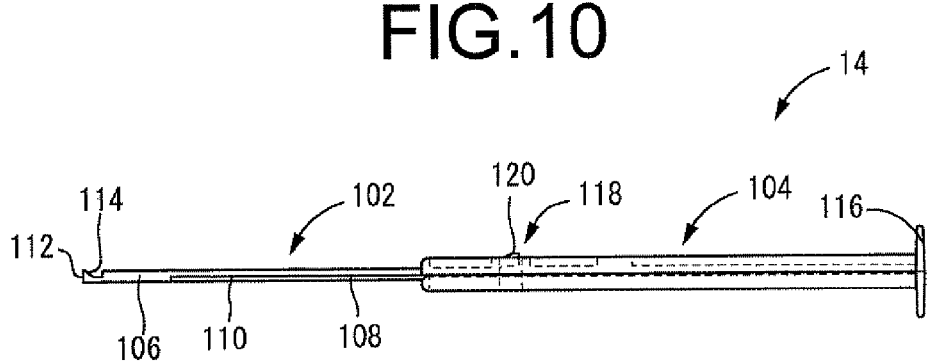
FIG. 10 is a side elevation of the same plunging member.

Then, the plunger 14, as a plunging member, is inserted into the through-hole 30 from the rear of the tool body 12 made in such a structure to be assembled thereto. FIGS. 9 and 10 show the plunger 14. The plunger 14 is formed with the same material as, for example, the tool body 12 and made in an approximate shape of a rod that has a slightly larger length in the axial direction than that of the tool body 12 in the axial direction, wherein an active part 102 in an approximate shape of a cylinder and an insertion part 104 in an approximate shape of a rectangular rod are integrally formed.

The active part 102 is configured to include the shaft section 106 in an approximate shape of a cylinder that extends along the central axis of the plunger 14 and flattened sections 108 in a form of a thin plate that extends out to both sides in the width direction of the shaft section 106. The flattened sections 108 extend out toward the tip from the rear end of the shaft section 106 with the same width as the insertion part 104, whereas a tapered portion 110 is formed with its width gradually reduced as it goes from approximately the middle part of the shaft section 106 in the longitudinal direction toward the position slightly back from the tip thereof. In this situation, the shape of the tapered portion 110 when viewed from above is designed to fit the horizontal cross-section of the intermediate section 76 at the through-hole 68 of the nozzle part 66.

The shaft section 106 is made to extend straight in the axial direction with a constant cross-section in an approximate shape of an oval, and the tip face of the shaft section 106 is made to be the lens pressing surface 112 extending in the axis-perpendicular direction of the shaft section 106. Such lens pressing surface 112 is formed with a dimension spanning from the bottom surface 84 to the upper surface 86 at least at the tip end section 78 of the nozzle part 66. Additionally, at the tip of the shaft section 106 in the axial direction, a cutout 114 is formed. In the present embodiment, the cutout 114 opens upward on the shaft section 106 and made in a form of a groove across the width direction of the shaft section 106, and the inner periphery thereof located in front in the axial direction is made to be an incline sloping upward as it goes toward the front in the axial direction, whereas the inner periphery located toward the back in the axial direction is made to be a vertical plane rising upward.

Meanwhile, the insertion part 104 is formed in a dimension slightly larger than that of the through-hole 30 in the axial direction. Such insertion part 104 is in an approximate cross-sectional shape of an H in its near entirety, and its width and height are made slightly smaller than those of the through-hole 30. Also, around the periphery of the end of the insertion part 104, a pressing plate 116 in a form of a disc is integrally formed extending in the axis-perpendicular direction.

In addition, slightly forward of the middle of the insertion part 104 in the axial direction, a latching section 118 is formed as a holding means. In the latching section 118, a tab 120 is formed protruding into the through-hole that runs through the insertion part 104 in the axis-perpendicular direction and protruding upward from the insertion part 104. Then, the plunger 14 is maintained in a state of being inserted with its position fixed relative to the tool body 12 by means of having the tab 120 engaged with an latching hole 122 made on top of the cylinder main body 28 to penetrate through in the thickness direction under the condition where the plunger 14 is inserted into the cylinder main body 28 of the tool body 12. Also, the positions where the tab 120 and the latching hole 122 are formed are set in such a way that the lens pressing surface 112 of the plunger 14 is slightly separated from the optical zone 18 of the intraocular lens 16 contained in the stage 34 in the plunging direction toward the back and the cutout 114 is positioned to support the haptic 20 located toward the back in the plunging direction from below. Meanwhile, the latching section 118 and latching hole 122 can be formed, for example, on the bottom or side of the insertion tool 10.

The intraocular lens insertion tool 10 structured as above is offered for use to the operator in an initial position condition where the tip of the plunger 14 is inserted into the cylinder main body 28 of the tool body 12 from the back and the tab 120 is latched in the latching hole 122.

Figure 11:
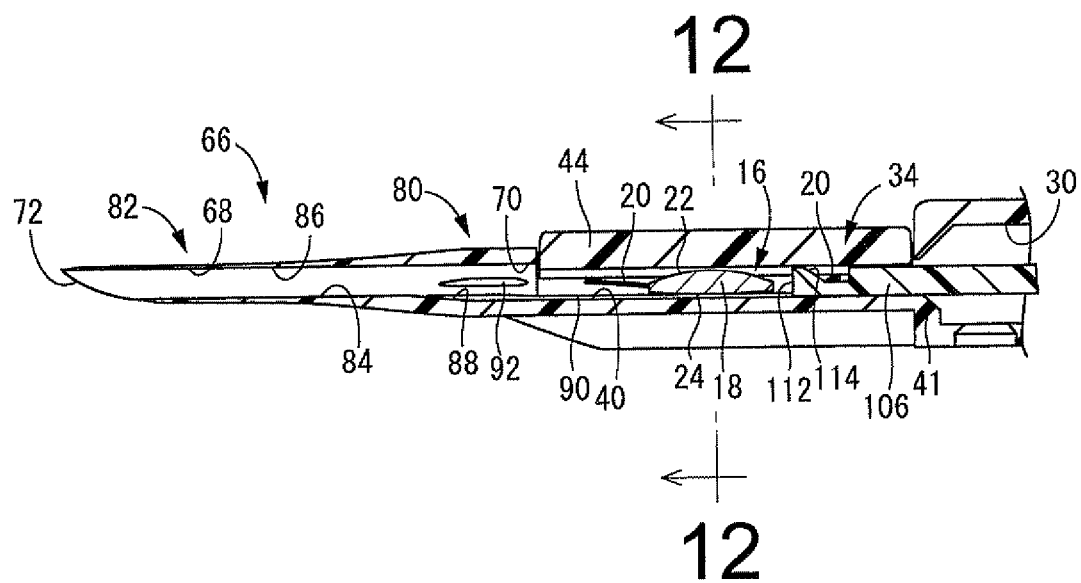
FIG. 11 is a section diagram explaining containment of the intraocular lens in the same insertion tool.
Figure 12:
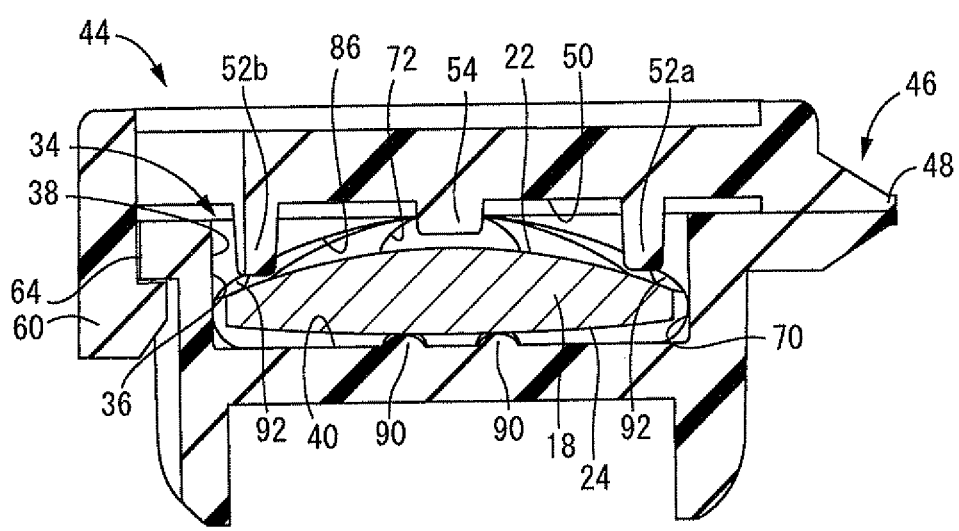
FIG. 12 is a section diagram cutting through 12-12 in FIG. 11.

Then, the intraocular lens 16 is placed on the lens platform 40 of the stage 34, where the cover section 44 had already been opened or is newly opened by the operator, in such a way that the rear surface of the optical zone 24 faces the lens platform 40. Thereafter, the hinge section 46 is bent and the opening 38 of the stage 34 is covered with the cover section 44. This allows the engaging tab 60 to be engaged with the engaging notch 64 so that the cover section 44 is maintained closed and, as shown diagrammatically in FIGS. 11 and 12, the intraocular lens 16 is set in containment within the tool body 12. In FIG. 12, the haptics 20 of the intraocular lens 16 are omitted.

Under such condition of placement on the lens platform 40, the optical zone 18 is positioned away from the lens pressing surface 112 of the plunger 14 set at its initial position toward the front in the plunging direction, while the haptic 20 located in the back in the plunging direction is contained in the cutout 114 to be supported by the bottom surface thereof. Also, since the width of the concave groove 36 is made only slightly larger than the diameter of the optical zone 18 of the intraocular lens 16, the intraocular lens 16 is prevented from rotating around the circumference on the lens platform 40. In addition, especially in the present embodiment, the center of the rear surface of the optical zone 24 of the intraocular lens 16 is made in contact with the guiderail 90 due to its extension all the way to the lens platform 40.

Meanwhile, a proper lubricant is to be poured into the stage 34 and nozzle part 66 via the liquid inlet 58 as necessary, with the cover section 44 remaining closed. However, the lubricant can be poured through the tip opening 72 of the nozzle part 66, through the opening 38 of the stage 34 with the cover section 44 opened, or through the rear opening of the through-hole 30 after pulling out the plunger 14 from the tool body 12.

Subsequently, the tip opening 72 of the nozzle part 66 is inserted into an incision made in the ocular tissue. In the present embodiment, since the tip opening 72 is in a slanted form, insertion into the incision can be done rather easily.

Then, the pressing plate 116 of the plunger 14 is pushed into the tool body 12 keeping the nozzle part 66 inserted into the incision. This makes the lens pressing surface 112 of the plunger 14 abut against the center of the outer periphery of the optical zone 18 of the intraocular lens 16 placed on the lens platform 40 so that the intraocular lens 16 is guided toward the base opening 70 by the plunger 14. In this situation, since the haptic 20 located on the side of the plunger 14 in the intraocular lens 16 is placed in the cutout 114 of the plunger 14, the lens pressing surface 112 of the plunger 14 is made to face directly with the outer periphery of the optical zone 18, thus avoiding a risk of involving the haptic 20 when having the lens pressing surface 112 abut against the optical zone 18.

Meanwhile, especially in the present embodiment, the cutout 114 is made in a shape of a concave groove that extends approximately in the width direction on top of the plunger 14, while the groove wall on the front side of the plunger 14 in the plunging direction is made to be an incline that spreads open to the opening side of the concave groove. This allows the haptics 20 of the intraocular lens 16 to be easily and securely placed into the cutout 114 in a concave groove form. Additionally, since the groove wall to the back of the plunger 14 in the plunging direction at the cutout 114 in a concave groove form is made to be an approximately vertical plane rising from the bottom of the groove toward its opening, the haptics 20 entered into the cutout 114 are effectively prevented from slipping out of the concave groove (cutout 114) during the push-out operation of the plunger 14 after being introduced securely into the cutout 114 at the incline on front side of the concave groove (cutout 114), thus being securely held in a state of insertion therein.

Then, by having the pressing plate 116 of the plunger 14 pushed in toward the tool body 12, the engagement between the tab 120 and the latching hole 122 is released, and the lens pressing surface 112 is made to abut against the center of the outer periphery of the optical zone 18. In this situation, the shaft section 106 of the plunger 14 is restricted from having excess displacement in the left-right direction by being sandwiched by guiding protrusions 56 and 56 formed in the cover section 44 from both sides of the tool body 12 in the width direction, and at the same time, from having excess displacement upward by being abutted against the central guide plate 54. This allows the shaft section 106 to be moved securely in the axial direction of the tool body 12. In addition, especially in the present embodiment, as shown by the imaginary line in FIG. 13A, the displacement of the shaft section 106 in the axial direction of the tool body 12 can be made more securely by having the shaft section 106 in contact with the pair of guiderails 90 on both sides of the tool body 12 in the width direction and guided in the axial direction thereof.

Also, since the central guide plate 54 and the right and left guide plates 52*a* and 52*b* installed on the cover section 44 are made to protrude toward the lens platform 40 with the cover section 44 remaining closed, excess upward displacement of the intraocular lens 16 is restricted, making it possible to smoothly guide the intraocular lens 16 into the base opening 70.

Figure 13A:
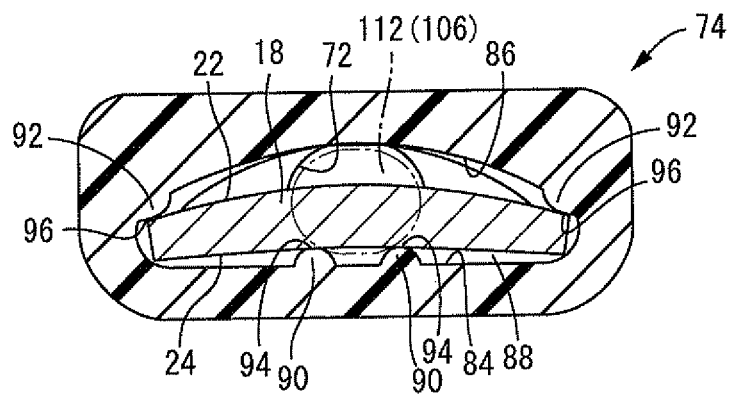
FIGS. 13A, 13B, 13C are sectional diagrams explaining deformation of the intraocular lens.

Then, the intraocular lens 16 sent into the introductory part 80 via the base opening 70, as shown diagrammatically in FIG. 13A, has the center of the rear surface of the optical zone 24 get in contact with the guiderails 90 made to protrude from the bottom surface 84, while siderails 92 protruding from the upper surface 86 are each in contact with both ends of the front surface of the optical zone 22 in the direction perpendicular to the plunging direction. This causes a stress exerting toward the upper surface 86 at the center of the rear surface of the optical zone 24, while causing another stress exerting toward the bottom surface 84 at both ends of the front surface of the optical zone 22 in the direction perpendicular to the plunging direction. As a result, the optical zone 18 of the intraocular lens 16 is deformed in a state of mountain fold wherein the front surface of the optical zone 22 is made convex toward the upper surface 86.

In this situation, the upper surface 86 is made to be curved in the introductory part 80, while the bottom surface 84 is made with larger ratio of curvature than the upper surface 86, or especially in the present embodiment, to be a flat plane with infinite ratio of curvature. This allows the cross-section of the through-hole 68 in the axis-perpendicular direction at the introductory part 80 to be made similar to the shape of the intraocular lens 16 in a state of mountain fold, which restricts the formation of excess space as much as possible and restricts the intraocular lens 16 from slipping into the excess space, while the intraocular lens 16 is able to follow the cross-section of the through-hole 68, thus enabling to produce mountain fold deformation more securely.

Additionally, in the present embodiment, the guiderails 90 are extended to the lens platform 40, and the guiderails 90 and the center of the rear surface of the optical zone 24 are in contact with each other from the time when the lens is placed on the lens platform 40. This makes it possible in advance to cause an appropriate mountain fold deformation of the optical zone 18 before it is sent to the introductory part 80, thus enabling to make a contact with the siderails 92 when the lens is sent to the introductory part 80 and produce mountain fold deformation more securely.

Then, the intraocular lens 16 that was subjected to initial deformation in a state of mountain fold in the introductory part 80 is sent to the tip opening 72 through the send-out part 82 to undergo smaller deformation. In this situation, when the tip of the plunger 14 reaches the intermediate section 76, a moderate sensation is felt by the operator due to the abutting of the tip of the plunger 14 against the incline 88 formed on the bottom surface 84. This allows the operator to be informed that the tip of the plunger 14 has reached the intermediate section 76, that is, the flexural deformation of the intraocular lens 16 has started.

Figure 13B:
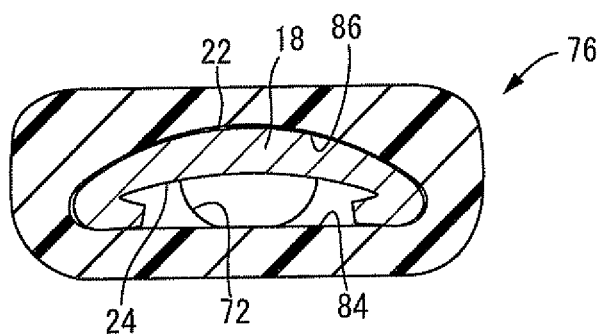
Figure 13C:
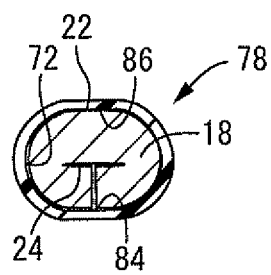

Then, the intraocular lens 16 that has undergone initial deformation in a state of mountain fold in the introductory part 80, as shown diagrammatically in FIG. 13B, is deformed to a smaller size as if being curled up as it passes through the intermediate section 76. In this situation, the optical zone 18 is deformed in line with the inside shape of the through-hole 68, with the state of mountain fold being further progressed, and the front surface of the optical zone 22 is curled up in a state of abutting against the upper surface 86. Then, the optical zone 18, as shown diagrammatically in FIG. 13C, is curled up to a smaller size in an approximate shape of an oval at the tip end section 78 of the nozzle part 66 in line with the through-hole 68 that is made in an approximate shape of an oval as it goes toward the tip.

In this situation, the haptic 20 positioned toward the front of the intraocular lens 16 in the plunging direction is forced to get into the curled up optical zone 18 as the optical zone 18 is curled up in line with the inside shape of the through-hole 68. This causes the state of tucking to occur in the intraocular lens 16 within the through-hole 68 as shown diagrammatically in FIG. 14.

Especially in the present embodiment, guiderails 90 and siderails 92 are terminated at a position slightly beyond the introductory part 80, and the send-out part 82 is almost entirely made to be a non-forming region of guiderails 90 and siderails 92. In other words, it is only necessary for the guiderails 90 and siderails 92 to cause initial deformation in mountain fold to the intraocular lens 16. In this situation, according to the present embodiment, it is made possible to avoid imposing excessive stress on the intraocular lens 16 reducing the risk of damaging it and to allow smoother push-out thereof by means of not forming any guiderails 90 or siderails 92 in the send-out part 82.

Figure 14:
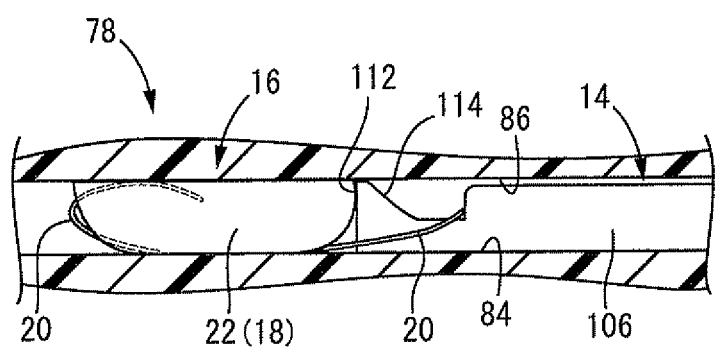
FIG. 14 is a sectional diagram explaining tucking of the intraocular lens.

Furthermore, as shown diagrammatically in FIG. 14, the lens pressing surface 112 is formed in a dimension spanning from the bottom surface 84 to the upper surface 86 at least at the tip end section 78 of the nozzle part 66. This, by making a mountain fold, makes the area of contact of the optical zone 18 with the lens pressing surface 112 to be floated from the bottom surface 84, and even if the area of contact, especially at the tip end section 78, with the lens pressing surface 112 reaches near the upper surface 86, the state of abutting between the lens pressing surface 112 and optical zone 18 can be maintained stably, thus enabling secure push-out of the intraocular lens 16 even in a state of mountain fold. However, as evident from the above description, it is only necessary for the lens pressing surface 112 to press on both the outer periphery of the optical zone 18 placed on the bottom surface 84 and the outer periphery of the optical zone 18 positioned on the side of the upper surface 86 in a mountain fold, and it is no problem if there is a gap smaller than the thickness of the outer periphery of the optical zone 18 between the lens pressing surface 112 and the bottom surface 84 or upper surface 86.

Then, the intraocular lens 16 is sent to the tip opening 72 of the nozzle part 66 maintaining such a state of tucking. In this situation, since the tip opening 72 is made in a slanted form, the intraocular lens 16 can be gradually exposed from the tip opening 72 while maintaining deformation, that is, according to the present embodiment, the state of tucking of the intraocular lens 16 for a longer period of time. This allows the intraocular lens 16 to be pushed out from the tool body 12 in the state of tucking and inserted into the capsule, and by restricting the preceding haptic 20 from contacting the interior of the capsule, the consequent risk of having the intraocular lens 16 reversed can be reduced.

Figure 15A:
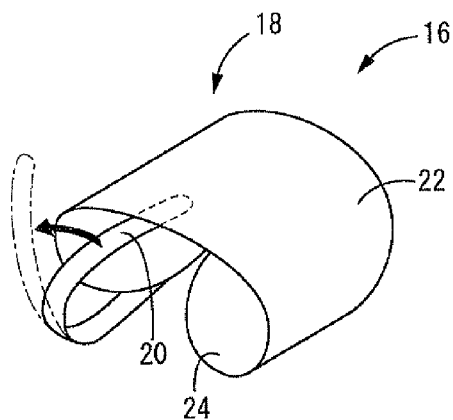
FIGS. 15A and 15B are diagrams explaining the unfolding direction of a haptic.
Figure 15B:
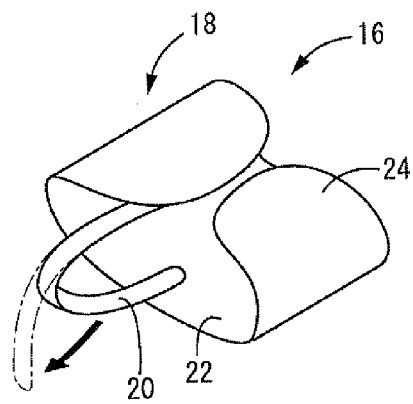

In addition, even when the haptic 20 unfolds and protrudes out prior to the optical zone 18 during the process of its exposure from the tip opening 72, as shown diagrammatically in FIG. 15A, the tip of the haptic 20 unfolds and protrudes out toward the front surface of the optical zone 22 on the upper side of the insertion tool 10. On the contrary, as shown diagrammatically in FIG. 15B, in the state of tucking in a valley fold, the tip of the haptic 20 unfolds and protrudes out toward the rear surface of the optical zone 24 on the lower side of the insertion tool 10. Therefore, by creating a state of tucking in a mountain fold, the haptic 20 is made to abut against the front side of the lens capsule (intracapsular front), which should normally happen, as compared to unfolding and protruding from a state of tucking in a valley fold, even when the haptic 20 unfolds and protrude prior to the optical zone 18, thus making it easy to avoid adverse effect on positioning of the intraocular lens 16. At the same time, the tip of the haptic 20 that unfolds and protrudes out from a state of tucking in a mountain fold does so with its front side (corresponding to the front side of the lens) facing forward in the travelling direction. On the contrary, the tip of the haptic 20 that unfolds and protrudes out from a state of tucking in a valley fold does so with its rear side (corresponding to the rear side of the lens) facing forward in the travelling direction. Therefore, at the tip of the haptic 20, its front side can be made to abut against the front side of the lens capsule more securely, which should normally happen, by being made to unfold and protrude out from the state of tucking in a mountain fold as opposed to the state of tucking in a valley fold. And, by having the optical zone 18 unfold as did the haptic 20 that was made in contact at the normal position, the optical zone 18 can be unfolded at the normal position more securely as opposed to the case of valley fold.

Thus, using the intraocular lens insertion tool 10 in the present embodiment, it becomes possible to create a state of tucking more securely by causing initial deformation more securely to the intraocular lens 16 in a mountain fold, and by inserting the intraocular lens 16 into the capsule under such tucking condition, it becomes possible to place the front surface of the optical zone 22 and rear surface of the optical zone 24 of the intraocular lens 16 at the normal position within the capsule more securely. As a result, it is rendered unnecessary to inversely rotate the insertion tool 10 as much as the operator anticipated, thus enabling easier and more secure insertion of the intraocular lens 16.

One of the embodiments of this invention has been explained above, which is just an example, and this invention is not to be interpreted in a limited sense by any specific description of such embodiment. In the following description, as to the members and parts with similar structures to those of the above embodiment, detailed explanations are omitted by applying the same reference numerals as those of the above embodiment to the figures.

For example, the lengths and end positions of the guiderails 90 and siderails 92 can be set as appropriate. For example, in the above embodiment, each front end of the guiderails 90 and siderails 92 protrudes forward slightly beyond the introductory part 80 in the plunging direction of the lens, and the rear ends of the guiderails 90 protrude out off the introductory part 80 toward the back in the same direction to be positioned on the lens platform 40, but this invention is not limited to such aspect. To give a more specific example, the front and back ends of both or either of the guiderails 90 and siderails 92 can be positioned within the introductory part 80 so that at least either of the guiderails 90 and siderails 92 are formed only within the introductory part 80, or even the rear ends of the siderails 92 can be made protruded from the introductory part 80.

Also, in the above embodiment, the pair of guiderails 90 and pair of siderails 92 are each formed approximately parallel to each other, and the separation distances to each other were set approximately constant across the entire length, but these distances can be varied along the longitudinal direction, or for example, the separation distance can be set slightly shorter in line with the tapered shape at the intermediate section 76 of the nozzle part 66. Therefore, at the rear end of the plunging direction, the separation distance between the guiderail 90 and siderail 92 in the up-down direction, for example, can be set larger than the separation distance B between the outer periphery of the front surface of the optical zone 22 and the apex of the rear surface of the optical zone 24 in the direction of optical axis of the lens. This allows the optical zone 18 to be guided more smoothly between both pairs of rails 90 and 92. Also, the protruding heights of these guiderails 90 and siderails 92 can be varied along the longitudinal direction.

Figure 16:
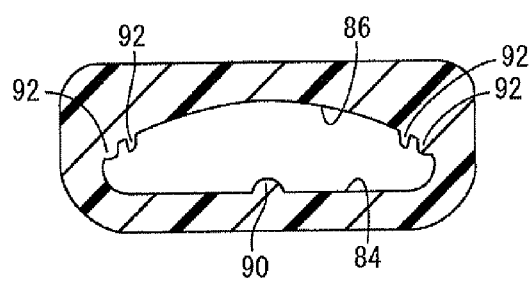
FIG. 16 is a section diagram explaining a different embodiment of this invention.

In addition, the number if central and lateral protrusions is not limited. In the above embodiment, for example, the central protrusion was formed by the pair of guiderails 90, but as shown diagrammatically in FIG. 16 for example, the central protrusion can be formed by a single guiderail 90 extending at the center in the width direction on the bottom surface 84. Moreover, also as shown diagrammatically in FIG. 16, one of the lateral protrusions can be formed by multiple siderails 92. In this situation, more preferably, the protruding dimension from the upper surface 86 toward the bottom surface 84 of the siderail 92 is made larger as it gets closer to the edge of the upper surface 86 in the width direction. This way, stress can be exerted on the intraocular lens 16 so as to produce mountain fold deformation more effectively.

Also, in the above embodiment, the guiding mechanism of the plunging member is configured to guide the plunger 14 with the pair of guiderails 90 in the axial direction, but such a mechanism is not necessarily essential, and the specific form of the guiding mechanism is not limited to the above embodiment. As shown diagrammatically in FIG. 16, for example, a single guiderail 90 extending at the center in the width direction on the bottom surface 84 can be formed as a central protrusion, whereas, by means of forming a concave groove that fits in with it on the undersurface of the plunger, which is not shown in the figure, the plunger can be guided in the axial direction by a guiding function of the concave groove and the guiderail 90.

Figure 17:
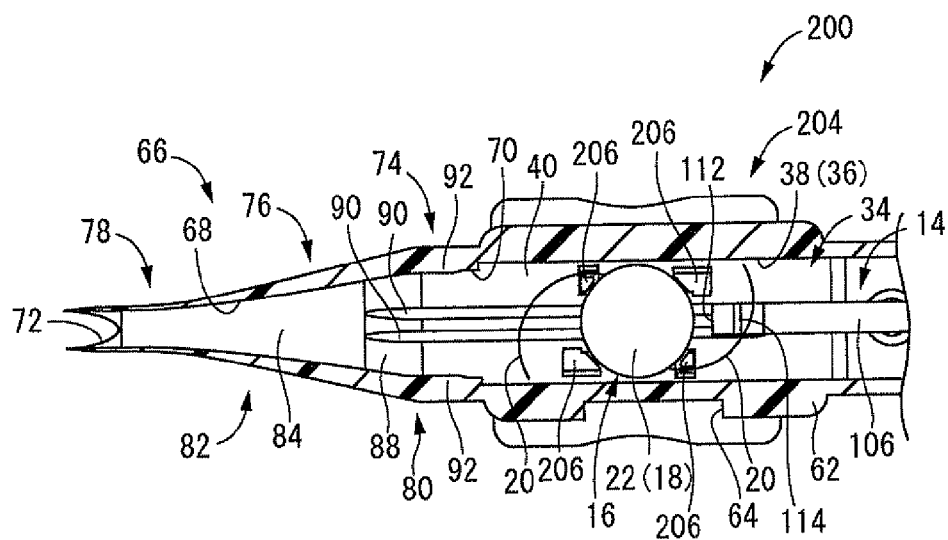
FIG. 17 is a horizontal section showing an insertion tool as a further different embodiment of this invention.
Figure 18:
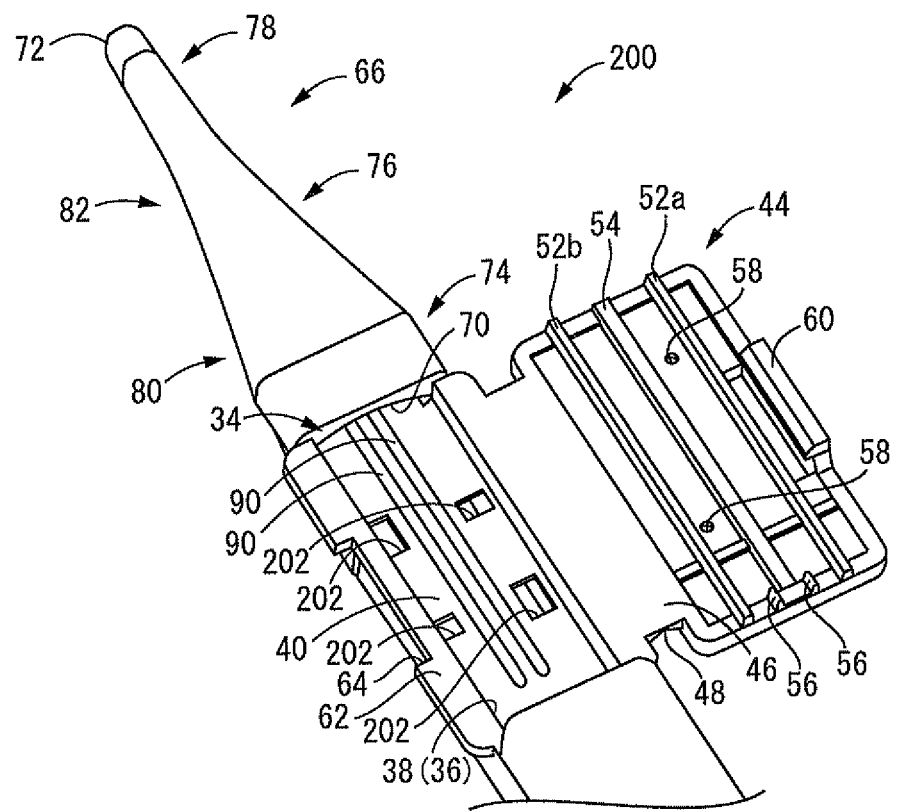
FIG. 18 is an enlarged axonometric view of a main part of the same insertion tool.

Meanwhile, in the above embodiment, as an intraocular lens insertion tool, a type of an insertion tool that contains in its tool body an intraocular lens prepared separately for the operation was described as an example, but as a matter of course, this invention is applicable to so-called "a preset type insertion tool" provided with an intraocular lens contained therein as shown diagrammatically in FIGS. 17 and 18. Here, FIG. 17 is shown with the cover section 44 omitted, and FIG. 18 is shown with a carrying member 204, to be explained later, removed. In an intraocular lens insertion tool 200 shown in FIGS. 17 and 18, a through-hole 202 is formed running through the tool body 12 at an appropriate location of the lens platform 40 and the carrying member 204 is assembled in a detachable manner from the opposite side of the lens platform 40 in the tool body 12. A carrying part 206 that supports the intraocular lens 16 is provided in such carrying member 204, while the carrying part 206 is made to protrude above the lens platform 40 via the through-hole 202 when assembled. Meanwhile, the carrying member 204 is kept assembled with the tool body 12 by means of engaging its tabs provided on the carrying part 206 with the lens platform 40.

The insertion tool 200 with the above structure is offered to the operator in a state of containing the intraocular lens 16 wherein the carrying member 204 is assembled to the tool body 12 and the intraocular lens 16 is carried by the carrying part 206 that is made to protrude above the lens platform 40 with the cover section 44 closed. Then, during the operation, by detaching the carrying member 204 from the tool body 12, the carrying part 206 is removed from the lens platform 40 so that the intraocular lens 16 is placed thereon. In this situation, according to the present aspect, wrong operations such as setting the lens with the front and back reversed on the stage 34 can be prevented by having the intraocular lens 16 preset in the carrying member 204 at the normal position where the rear surface of the optical zone 24 faces the lens platform 40.

Also, especially the insertion tool 200 in the present aspect has guiderails 90 extend further back compared to the above embodiment all the way to the lower part of the tip of the plunger 14 that was set as an initial position. This allows, according to the present aspect, the plunger 14 to be guided in the axial direction of the tool body 12 from the outset of the push-out operation, thus enabling stable push-out of the plunger 14.

Meanwhile, to verify the efficacy of this invention, insertion tools structured according to the above embodiment as working examples and other insertion tools having no lateral protrusions with other configurations made equal to the working examples as comparative examples were prepared, and for each of these working and comparative examples, push-out operations of the intraocular lens were conducted setting the power at +6.0 D, ratio of curvature on the front surface of the optical zone at about 50 mm, ratio of curvature on the rear surface of the optical zone at about 70 mm, and the directions of deformation of the intraocular lens were observed. As a result, as to the comparative examples, two out of thirty examples were deformed in a valley fold, and one example was deformed in an S shape where a mountain fold and valley fold coexist, whereas, as to the working examples, all 30 examples were deformed in a mountain fold. This proved that the mountain fold deformation of the intraocular lens can be generated more securely according to this invention.

The invention claimed is:

1. An intraocular lens insertion tool comprising:
an intraocular lens;
a tool body in a form of a cylinder adapted to contain the intraocular lens;
a plunging member to be assembled to the tool body by being inserted therein in an axial direction from a back;
a stage on which the intraocular lens is adapted to be placed provided at a middle of the tool body in the axial direction; and
an insertion cylinder of tapered shape on a tip side of the stage in the axial direction, the plunging member being adapted to be plunged in order to move forward the intraocular lens placed on the stage in the axial direction so that the intraocular lens is deformed compactly and pushed out through the insertion cylinder into an eye, wherein:
the stage includes a lens platform that extends in an axis-perpendicular direction of the tool body, and the intraocular lens is placed on the lens platform with a rear surface of an optical zone thereof facing the lens platform while not being folded;
the insertion cylinder includes a bottom surface continuous from the lens platform of the stage, and an upper surface placed opposite the bottom surface;
a central protrusion is provided at a central portion in a width direction of the tool body in the bottom surface of an introductory part on a side of the stage of the insertion cylinder so as to extend in the axial direction of the tool body and be made to protrude toward the upper surface to get in contact with a center portion of the rear surface of the optical zone of the intraocular lens sent into the insertion cylinder;
a pair of lateral protrusions are provided at both ends in the width direction of the tool body in the upper surface of the introductory part so as to extend in the axial direction of the tool body and be made to protrude toward the bottom surface to get in contact with both ends of a front surface of the optical zone of the intraocular lens sent into the insertion cylinder;
the plunging member has a lens pressing surface formed at a tip face thereof in the axial direction with a dimension spanning from the bottom surface to the upper surface at a tip end section of the insertion cylinder; wherein
when the intraocular lens is inserted into the insertion cylinder, the central protrusion comes into contact with the center portion of the rear surface of the optical zone of the intraocular lens, while the pair of lateral protrusions come into contact with the both ends of the front surface of the optical zone of the intraocular lens so that the optical zone of the intraocular lens is subject to initial deformation in a mountain shape where the front surface of the optical zone is made convex.

2. The intraocular lens insertion tool according to claim 1, wherein a tip opening of the insertion cylinder has an inclined shape wherein the upper surface protrudes beyond the bottom surface in the axial direction of the tool body.

3. The intraocular lens insertion tool according to claim 1, wherein a separation distance between the pair of lateral protrusions at their protruded tips in the width direction of the tool body is smaller than an outer diameter of the front surface of the optical zone of the intraocular lens at a tip of the lateral protrusions in a plunging direction of the intraocular lens, and a separation distance between the central protrusion and the lateral protrusions in a facing direction of the upper surface and the bottom surface is smaller than a separation distance between an outer periphery of the front surface of the optical zone of the intraocular lens and an apex of the rear surface of the optical zone in a direction of an optical axis at a tip of the central protrusion in the plunging direction of the intraocular lens.

4. The intraocular lens insertion tool according to claim 1, wherein a reduction rate of an area per length in the axial direction at the insertion cylinder is varied along the axial direction, and an intermediate section in the axial direction of the insertion cylinder is formed with the largest reduction rate of the area, while a width of the bottom surface at the intermediate section is made to gradually vary from a dimension larger than an outer diameter of the intraocular lens down to smaller dimensions, and the central protrusion and the pair of lateral protrusions are formed to extend in the axial direction from an axial end on a side of larger width at the intermediate section, the introductory part being configured to include a part of the intermediate section.

5. The intraocular lens insertion tool according to claim 4, wherein tips of the central and lateral protrusions in a plunging direction of the intraocular lens are positioned at the intermediate section.

6. The intraocular lens insertion tool according to claim 1, wherein a curvature radius of the bottom surface is larger than that of the upper surface at the introductory part.

7. The intraocular lens insertion tool according to claim 6, wherein the bottom surface at the introductory part is a flat plane.

8. The intraocular lens insertion tool according to claim 1, wherein a rear end of the central protrusion in a plunging direction of the intraocular lens extends to the lens platform.

9. The intraocular lens insertion tool according to claim 1, wherein the central protrusion guides the plunging member in the axial direction of the tool body by getting in contact with the plunging member.

10. The intraocular lens insertion tool according to claim 9, wherein the central protrusion comprises a pair of guiderails, positioned on both sides of the plunging member in the width direction of the tool body, and at tips of the guiderails in a plunging direction of the intraocular lens, a separation distance between the guiderails at their protruded tips in the width direction of the tool body is smaller than a separation distance between the pair of lateral protrusions at their protruded tips in the same direction.

\* \* \* \* \*